United States Patent [19]

Ebeling

[11] 4,376,629
[45] Mar. 15, 1983

[54] FLEXIBLE DENTURES

[76] Inventor: Edwin Ebeling, 2706 E. 57th St., Long Beach, Calif. 90805

[21] Appl. No.: 307,193

[22] Filed: Oct. 1, 1981

[51] Int. Cl.³ .............................................. A61C 13/08
[52] U.S. Cl. ..................................... 433/200; 433/193
[58] Field of Search ............... 433/200, 209, 210, 171, 433/205, 193

[56] References Cited

U.S. PATENT DOCUMENTS 2,817,900 12/1957 Glasser ................................. 433/200

FOREIGN PATENT DOCUMENTS 136489 12/1919 United Kingdom ................ 433/171

Primary Examiner—Robert Peshock

[57] ABSTRACT

Dentures are formed having a spring steel frame with a curved base and on one side of which pairs of diverging flanges extend at missing tooth positions. Barbed pins extend through the base at the missing tooth positions, and the frame is encased in a resilient, flexible plastic which is molded and colored to resemble the gums of a wearer. Artificial teeth are impaled on the barbed pins. The denture is a generally horseshoe shaped structure which provides a flexible support for the artificial teeth. The diverging flanges of the frame are resiliently deformed so as to grip the gums of a wearer when the dentures are worn. The upper denture requires no stabilizing structure extending across the roof of the mouth of a wearer.

10 Claims, 6 Drawing Figures

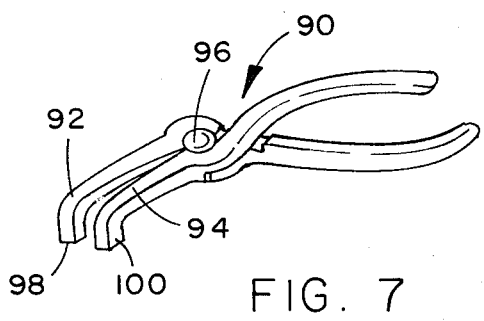
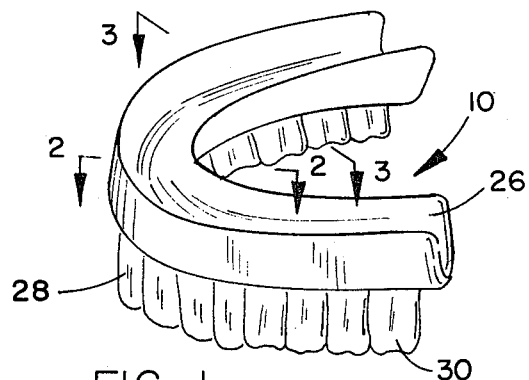
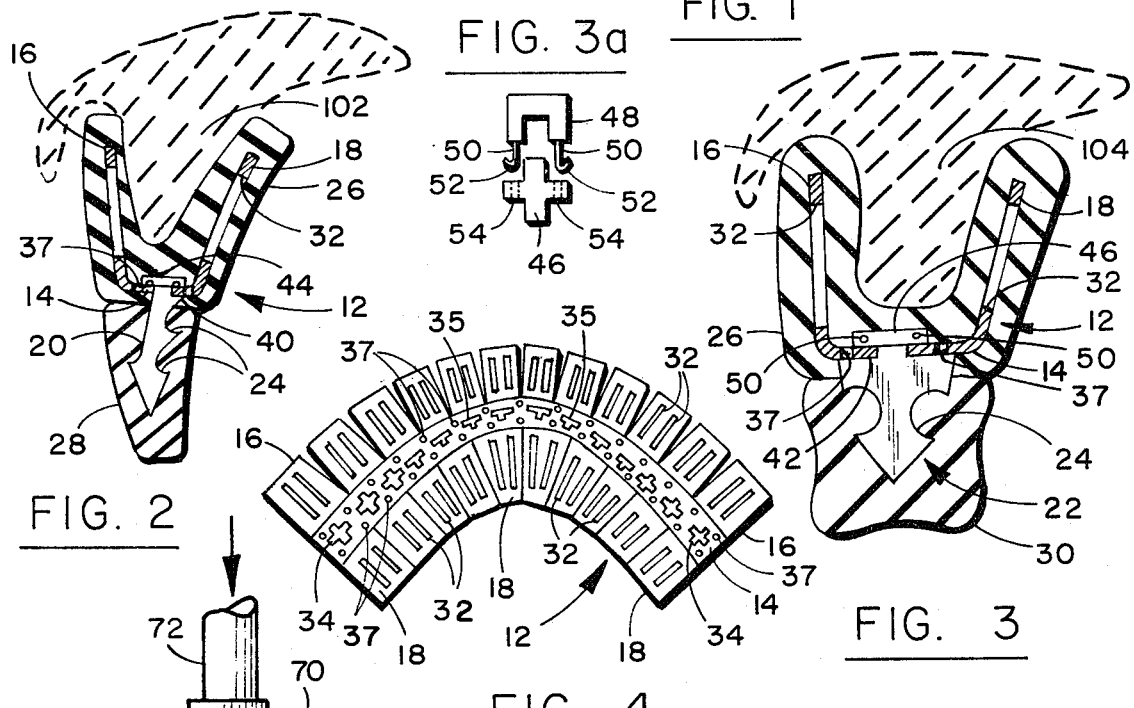
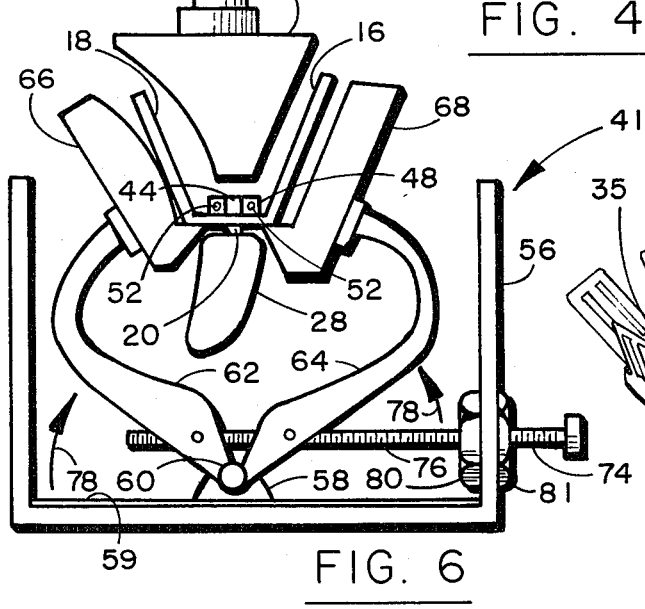
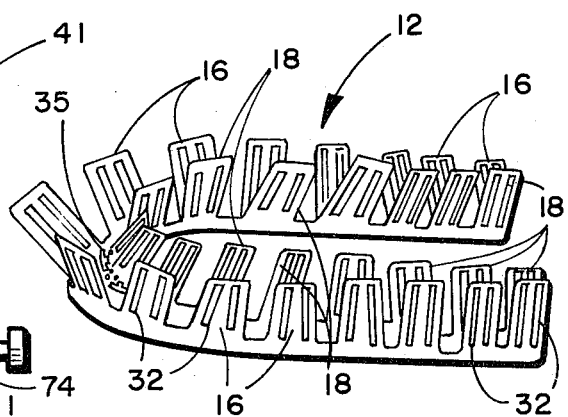

FLEXIBLE DENTURES

BACKGROUND OF THE INVENTION

1. Field of the Invention

The present invention relates to dentures which bear artificial teeth to replace missing teeth of a wearer.

2. Description of the Prior Art

Numerous denture structures have been developed through the years to provide a wearer with artificial teeth to replace teeth which are missing through accident or disease. Conventional dentures have a rigid supporting foundation which is shaped and colored to resemble the gums of a wearer and which supports hard, artificial teeth. Although attempts have been made throughout the years to make dentures more comfortable to wear, genuinely comfortable dentures have not heretofore been achieved. Furthermore, dentures designed for wear to replace upper teeth have typically required a stabilizing web or other support structure that extends across the roof of the wearer's mouth. This structure adds to the discomfort of conventional dentures and reduces taste sensitivity of the wearer.

SUMMARY OF THE INVENTION

The present invention involves a flexible denture which employs a spring steel frame that has a curved base which is generally U-shaped. On one side of the base pairs of diverging flanges extend outwardly at each missing tooth position. Pins having barbs on the extremities thereof are secured to the base at holes therein and extend to the side of the base opposite the flanges at each missing tooth position. The frame is encased within a resilient, flexible, plastic coating. Artificial teeth are impaled upon the barbed pins so that the teeth are held on the pins in abutment against the plastic coating by the pin barbs.

A denture produced according to the invention provides the hard teeth with a flexible supporting structure which conforms comfortably to the gum line of a wearer. Although the structure which carries the artificial teeth is flexible, it does not twist in the mouth of the user as the user eats because the underlying jawbone and gum structure of the user provide the necessary rigidity of support.

Since the dentures of the invention are flexible, they conform to the shape of the user's gums, and thereby greatly reduce discomfort to the user. Also, because the dentures of the invention conform to the shape of the user's gum line they adhere strongly to the wearer's gums through the use of conventional denture adhesive. Furthermore, because the tooth supporting structures of the dentures of the invention flex with mastication, they provide a massaging action to the wearer's natural gums.

Although the dentures of the invention are lightweight, their flexibility and resiliency reduce the likelihood of breakage. The resilient plastic coating on the underlying spring steel frame resembles the natural gums of a wearer in appearance, texture, reflectivity and depth to a greater degree than do conventional dentures. Furthermore, the flanges of the spring steel frame are suited to immediate, individual adjustment for fitting and comfort. That is, the flanges are arranged to diverge from the frame base so that they tend to grip the wearer's gums therebetween, when properly adjusted. If the grip is too harsh or to loose, the angle of divergence between flanges at each missing tooth position can be adjusted by inelastically bending the flanges relative to the frame base. Such an adjustment can be performed with a tool which operates like a pliers but has gripping fingers suitable for inelastically deforming the encased flanges. Because the plastic coating on the frame is resilient, it accommodates such adjustment of the encased frame. Adjustment may be performed either by a dentist or by the wearer of the dentures himself.

A further advantageous feature of the dentures of the invention is that because they are readily adjustable to individual wearers, they provide more natural, individual, and life-like spacing between the teeth.

Incident to use, the dentures of the invention are provided with tubes of the curable plastic of which the coating on the frame is formed. Should lacerations of the flexible plastic coating occur, small quantities of the curable plastic can be squeezed into the lacerated area of the denture of the invention so that repair is easily achieved.

The flexible dentures of the invention adapt to the shape of a wearer's mouth and can be worn more comfortably and for longer periods of time than conventional dentures. In addition, because of the greater adhesion to the wearer's gums achieved with the flexible dentures, the artificial teeth can be cleaned in the user's mouth with a toothbrush in the natural manner in which real teeth are cleaned. The wearer is thereby not subjected to embarrassment in certain social situations, such as when visiting friends or relatives or in a communal type environment, such as the armed forces.

According to the method of manufacture of the invention a male denture mold portion is constructed from an impression of the gum line of the intended wearer. This male denture mold portion conforms to the gum line of the denture wearer. A female mold portion is configured to yield an impression which simulates the appearance of a gum line. The spring steel frame of the denture of the invention is mass produced with one millimeter variations. The spring steel frame is die cut from lightweight spring steel stock. Apertures are defined in the flanges and in the frame base at the positions corresponding to the missing tooth positions. Pins with barbs at their extremities are inserted into the apertures in the frame base and the heads of the pins are secured with clips so that the pins are securely held to the frame at the apertures. The apertures are especially configured in a certain geometric shape, such as a cruciform, and the pinheads are similarly shaped. This prevents the pins from turning in the apertures.

In manufacturing the dentures of the invention a patient's mouth is first measured for size, curvature and teeth placement. Measurement may be accomplished by making a cast of an impression of the gums of the patient. A patient bites down into a gel disposed on a plastic form of a size which fits into a patient's mouth. The gel retains the impression of existing teeth. A transparent sheet overlay printed with a graphic pattern that is colored with "best fit curves" is then pressed into the cast. The markings on the curves indicate the placement of the original teeth and provide an instant measurement of the size and curvature of the patient's mouth.

Measurement of the patient's teeth may also be facilitated by molding a metric aluminum strip around the circumference of the denture line. This strip is centered at the incisor midline. The strip is then placed on a graphic measuring card upon which dimensions are then marked.

Whatever the form of measurement, the measurements or templates derived are used to produce a bench plate former. The bench plate former is essentially a segmented vise capable of reshaping the configuration of the metal frame. The bench plate former includes configured mating jaws which inelastically deform the metal flanges of the frame in a calibrated and controlled manner. The structures upon which the jaws are mounted are also arranged for lateral movement to accommodate different patient jaw configurations.

The spring steel metal frame of the denture of the invention is covered with a soft plastic coating which is more natural in appearance and has a more lifelike texture than conventional denture plate structures. The plastic can be colored while in a liquid form to more closely match the flesh tones of an individual users mouth.

The invention may be described with greater clarity and particularity by reference to the accompanying drawings.

DESCRIPTION OF THE DRAWINGS

FIG. 1 is a perspective view of a denture according to the invention.

FIG. 2 is an elevational section taken along the lines 2—2 of FIG. 1.

FIG. 3 is an elevational section taken along the lines 3—3 of FIG. 2.

FIG. 3a is a plan detail of one aspect of construction of the denture of the invention.

FIG. 4 is a plan view of the spring steel frame of the denture of the invention before bending.

FIG. 5 is a perspective view of the spring steel frame at an intermediate stage of bending.

FIG. 6 is an elevational view of the incisor segment of the bench plate former as it is used to shape the spring steel frame of FIG. 5.

FIG. 7 is a perspective illustration of a tool useful in final fitting and adjusting the denture of the invention to individual patients.

EMBODIMENT AND METHOD OF CONSTRUCTION

FIG. 1 illustrates a denture 10 constructed according to the invention. The denture 10 has a spring steel frame 12, illustrated in isolation in FIG. 5. The spring steel frame 12 has a curved generally U-shaped base 14 on one side of which pairs of exterior flanges 16 and interior flanges 18 extend in diverging fashion at each tooth position. Pins, such as the pins 20 and 22, depicted respectively in FIGS. 2 and 3, are secured to the base 14 on the side thereof opposite the side from which the flanges 16 and 18 extend. Each pin 20 and 22 has at least one barb 24 at its extremity. As best illustrated in FIGS. 1, 2 and 3 a resilient, flexible, plastic coating 26 encases the spring steel frame 12. Hard surfaced artificial teeth, such as the teeth 28 and 30 depicted in FIGS. 2 and 3, are held fast to the frame 12 by the barbs 24 on the pins 20 and 22. The artificial teeth 28 and 30 are thereby held on the pins 20 and 22 in abutment against the plastic coating 26 by the barbs 24.

As illustrated in FIGS. 4 and 5, the spring steel frame 12 is die cut from spring steel stock and slot-like apertures 32 are defined in the flanges 16 and 18. Cruciform apertures 34 and T-shaped apertures 35 are defined in the U-shaped base 14 at each missing tooth position.

The frames 12 are die cut from flat, spring steel stock by an automatic die cutting machine. The die cutting machine slices lines of demarcation between adjacent flanges and also cuts the apertures 32, 34 and 35, as well as small circular apertures 37 in the base 14.

A segmented bench press 41 is used to inelastically deform the frame 12, as depicted in FIG. 6. When inelastically deformed the flanges 16 and 18 reside in pairs at divergent angles relative to each other, as depicted in FIGS. 2 and 3.

Once the spring steel frame 12 of FIG. 5 has been formed, the pins, such as the pins 20 and 22 are inserted into the cruciform apertures 34 from the side of the base 14 opposite the side from which the flanges 16 and 18 extend. Each of the pins 20 and 22 has a shoulder, depicted, respectively, at 40 and 42 in FIGS. 2 and 3.

All of the apertures 34 and 35 in the frame base 14 are non-circular cross section and are formed as geometric figures with at least some reentering angles. The apertures 35 which receive the pins 20 of the artificial incisors and front teeth 28 are of a T-shaped cross section. The heads 44 of the pins 20 are likewise of a T-shaped cross section and fit snugly into the apertures 35 so as to prevent rotation of the teeth 28 relative to the frame base 14.

The apertures 34 in the frame base 14 are shaped as cruciforms, and the pinheads 46 of the teeth 30 are of a corresponding geometric configuration to prevent any rotational or wobbling movement of the artificial teeth 30 relative to the frame base 14.

The pinheads 44 and 46 are secured in immobile fashion relative to the frame 12 by means of a particular type of cotter pin 48 depicted in FIG. 3a. The cotter pin 48 is of a U-shaped configuration and has a pair of parallel legs 50 with resilient, out turned tips 52. As with all cotter pins, the legs 50 are separate from each other and the tips 52 thereof spread after being pushed through parallel, lateral apertures 54 in the pinheads 44 and 46. The tips 52 of the cotter pin legs 50 prevent withdrawal of the cotter pin 48 from the pinhead once the tips 52 emerge from the structure of the pinheads and spread.

In manufacturing the denture 10, it is first necessary to determine the size and curvature of a patient's mouth and to ascertain tooth placement in the patient's mouth. In a typical method of obtaining the necessary measurements, a cast of an impression of the gums of an intended wearer is taken in a gel that retains the imprint of existing teeth. The bench plater former 41 is then constructed to conform to the cast. FIG. 6 illustrates the incisor segment of the bench plate former 41 utilized to produce the denture 10. The bench plate former 41 utilizes a generally U-shaped mounting frame 56. The U-shaped frame 56 is articulated into several segments, one of which is depicted in FIG. 6, and all of which are capable of reshaping the configuration of the metal frame 12.

Each segment of the bench plate former 41 includes a fulcrum pedestal 58 which rides in a track between two parallel ribs 59 extending transversely across the floor of the mounting 56. At the apex of the pedestal 58 there is a fulcrum 60 upon which a pair of arms 62 and 64 are mounted in opposing fashion. The arms 62 and 64 carry contoured molding jaws 66 and 68 at their free extremities. The facing surfaces of the jaws 66 and 68 are contoured to impart the desired shape to the mating flanges 16 and 18 of the frame 12 which are to be inelastically bent therein. Together the jaws 66 and 68 form bearing surfaces against which the flanges 16 and 18 are pressed and inelastically deformed. A ram 70 is raised and lowered by means of push rods 72 to press the flanges 16 and 18 against the jaws 66 and 68.

An adjustment screw 74 extends laterally through an oversize aperture in one of the walls of the mounting 56 to pass transversely above the pedestal 58. The adjustment screw 74 has a threaded shank 76. The shank 76 is received in interiorly threaded gimbals. The gimbal in the arm 62 is threaded in the opposite direction from the gimbal in the arm 64 so that when the adjustment screw 74 is turned in one direction, the arms 62 and 64 are drawn toward each other as indicated by the directional arrows 78 in FIG. 6. When the adjustment screw 74 is turned in the opposite direction, the jaws 62 and 64 are pushed away from each other in the directions opposite the directional arrows 78. Adjustment nuts 80 and 81 on the threaded shank 76 are employed to hold the jaws 66 and 68 at a selected position above the floor of the mounting 56.

It is to be understood that the mounting 56 is of a generally horseshoe shaped configuration and that several pairs of arms 62, 64 and jaws 66, 68 are mounted along its length. Each pair of arms 62, 64 has a separate adjustment screw 74. Each pair of arms 62, 64 operates a separate set of jaws 66, 68, and each set of jaws 66, 68 should be used to deform no more than two pairs of flanges 16, 18. Consequently, to inelastically deform the frame 12 depicted in FIG. 4, the mounting 56 preferably contains six sets of arms 62, 64, arranged at spaced intervals within the horseshoe shaped mounting 56.

To construct the denture of the invention the size and the curvature of a patient's mouth and teeth placement are first determined. As previously explained, this can be accomplished by making a cast of an impression of the gums of an intended denture wearer or by taking measurements of the contour of a patient's mouth and transferring these measurements to a graphic measuring card from which the dimensions of the frame 12 prior to deformation, as depicted in FIG. 4, are taken.

Either manner of measurement may be utilized for the configuration depicted in FIG. 4. The flexible denture frame 12 is die cut from light weight spring steel in the form shown in FIG. 4. The sizes and separations between the flanges 16 and 18, and the size and curvature of the base 14 are determined by the measurements taken of the prospective wearer's mouth. The flanges 16 and 18 in the vicinity of the wearer's incisor area are cut in a somewhat elongated, rectangular form, rather than in the more nearly square form in the molar area. This aids in providing the proper size and curvature of the flanges in the incisor area where the flanges extend toward the roof of the patient's mouth.

Once the frame 12 has been die cut in the template form depicted in FIG. 4, it is placed in the bench plate former 41 depicted in FIG. 6. The position of each pair of jaws 66, 68 is adjusted by turning the adjustment screw 74 to bring the jaws 66 and 68 to the desired separation, and by selectively positioning the nuts 80 and 81 relative to the shank 76 of the adjustment screw 74. The adjustment nuts 80 and 81 are first loosened so that the adjustment screw 74 can be moved laterally relative to the mounting 56, with the pedestal 58 for each pair of arms 62, 64, sliding in the track defined between the two parallel ribs 59 associated therewith. When the pedestal 58 is at the desired position along the track defined between the ribs 59, the nuts 80 and 81 are tightened to clamp the adjustment screw 74 to the wall of the mounting 56 and to lock the pedestal 58 at a desired position of translocation on the floor of the mounting 56.

Once the bench plate former 41 has been adjusted so that the jaws 66 and 68 conform to the configuration of the wearer's mouth, the frame 12 is placed in its flat form as die cut in FIG. 4 atop the jaws 66 and 68. The push rods 72 carrying the ram 70 are then forced toward the mounting 56 to inelastically deform the flanges 16 and 18 to the curvature defined by the jaws 66 and 68 and the ram 70.

Initially, the flanges 16 and 18 in the molar region are closed to the proper orientation on the bench plate former 41 and the incisor-roof flanges 18 are deformed into the proper curvature. The flanges 16 in the incisor area are bent upwards as well, but not completely since this would render attachment of the pins bearing the artificial teeth inordinately difficult. Rather, the frame 12 is bent to the intermediate configuration of FIG. 5.

The artificial teeth 28 and 30 are individually molded of ceramic and cured in a small gas furnace. The structural support pins 20 and 22 are inserted into the artificial teeth 28 and 30 respectively while the artificial teeth 28 and 30 are in a viscous, preheated stage. The alignment of the support pins 20 and 22 relative to the artificial teeth 28 and 30 is checked prior to heating the ceramic teeth 28 and 30.

Once the artificial teeth 28 and 30 have been cured, they are individually mounted upon the support pins 20 and 22 and are held on the support pins by the barbs 24.

Thereafter, the artificial teeth 28 and 30 are secured to the flexible metal frame 12. That is, the heads 44 and 46 of the pins 20 and 22, respectively, are respectively forced into their associated T-shaped apertures 35 and cruciform apertures 34 in the base 14 of the metal frame 12. The pinheads 44 and 46 protrude above the concave surface at the base 14 of the metal frame 12. Because of the particular geometric configuration of the pinheads 44 and 46 and the mating apertures 35 and 34, the teeth 28 and 30 will not swivel or turn relative to the metal frame 12.

The pinheads 44 and 46 are locked in position by insertion of the specially designed cotter pin 48 depicted in FIG. 3a. That is, the metal legs 50 of the cotter pin 48 are pressed into the parallel apertures 54 both in the pinheads 46 depicted in FIG. 3a, as well as into corresponding apertures in the pinheads 44 in an analogous manner. Once the tips 52 of the legs 50 emerge from the structure of the pinheads, they spring outwardly, thereby locking the pinheads 44 and 46 onto the base 14 of the metal frame 12. The shoulders 40 and 42 of the support pins 20 and 22, respectively, abut against the underside of the base 14 of the metal frame 12 and accept the force of biting and chewing once the dentures have been completed and are used.

A small space, approximately one millimeter, is left between the ceramic portion of the teeth 28, 30 and the underside of the base 14 of the metal frame 12. This space provides for the subsequent forming and adhesion of the soft plastic material simulating the wearer's gums.

Once the artificial teeth 28 and 30 are secured to the metal frame 12, the metal frame 12 is again placed into the bench plate former 41. The jaws 68 in the incisor area are then brought into the final forming position, and the outer flanges 16 in the incisor area are pushed into a generally upright position, as depicted in FIG. 6. The use of the bench plate former 41 a second time also serves to correct any minor distortions to bending of the flanges 16 and 18 which may have occurred during the process of inserting and securing the pins 20 and 22 to the frame 12. The second time that the frame 12 is inserted into the bench plate former 41, final adjustments are made to the flanges 16 and 18 to ensure proper alignment.

After the spring steel frame 12 has been shaped to its proper configuration, the soft, flexible, resilient plastic material is coated onto the frame 12 and molded in a mold. The plastic material forms the resilient coating 26 on the spring steel frame 12. The coating 26 penetrates the apertures 32 in the flanges and the apertures 37 in the base 14 of the frame 12. This provides a more secure adhesion between the metal of the frame 12 and the plastic material of the coating 26.

The plastic material also coats the interstices between the artificial teeth 28 and 30 and the underside of the base 14 of the frame 12. The coating 26 surrounds the portions of the pins 20, 22 adjacent the underside of the base 14, and the artificial teeth 28 and 30 reside in abutment against the coating 26 adjacent thereto.

The bottom half of the mold used to form the coating 26 is of the standard type used in producing artificial dentures. The upper half is an inverse mold made from a cast of the patient's mouth. The soft plastic material used to form the artificial gums is injected into the mold around the frame 12 in a semi-liquid state, and is allowed time to cure and set. Heat is applied to accelerate curing, if necessary.

Due to the resilient, soft nature of the plastic coating 26, the artificial gums have a more natural and life-like texture, reflectivity and depth. The color tone of the coating 26 can be individually adapted to a user's complexion and mouth coloring by dye introduced into the plastic in its semi-liquid state prior to curing. Also, the soft plastic coating 26 is much more comfortable to the denture wearer than are the rigid materials from which conventional dentures are formed. Furthermore, because the frame 12 is also flexible, the denture 10 much more readily adapts itself to the contour of the wearer's mouth, and the denture 10 can be worn for much longer periods of time as compared with conventional dentures.

After the denture 10 has cured, final adjustments are performed by bending the flanges 16 and 18 within the coating 26 as required to conform the denture 10 to the mouth of the intended wearer. A specially configured pair of pliers 90 are employed for this purpose. The pliers 90 are formed with arcuately curved mating portions 92 and 94 adjacent the hub of rotation 96. The curved portions 92 and 94 terminate at right angles in straight, flat, mating portions 98 and 100, all as depicted in FIG. 7. The flat portions 98 and 100 of the pliers 90 are used to grip the flatter portions of the flanges 16 and 18 within the coating 26 while the curved portions 92 and 94 are for the incisor-roof area of the flanges 18.

As illustrated in FIGS. 2 and 3, the flanges 16 and 18, although shaped to conform to the gums 102, 104 of the denture wearer, are also formed so as to grip the wearer's gums therebetween when worn. When a conventional denture adhesive is applied to the concave portion of the coating 26, the flexible nature of the frame 12 and the softness of the coating 26 allow the denture 10 to be worn for extended periods of time. Use of a denture 10 is not accompanied by nearly as much discomfort as occurs with conventional dentures, and the use of the gripping flanges 16 and 18 aids in maintaining a secure adhesion to the gums 102 and 104.

Undoubtedly numerous variations and modifications of the invention will become apparent to those familiar with denture construction. Accordingly, the scope of the invention should not be construed as limited to the specific embodiment and implementation depicted and described herein, but rather as defined in the claims appended hereto.

I claim:

1. A denture comprising a frame formed from flat spring steel stock and having a curved base from one side of which pairs of diverging flanges extend at each tooth position, pins secured to said base and extending therethrough to the opposite side thereof at each missing tooth position through configured apertures in said base which prevent said pins from rotating relative to said base, each pin having at least one barb thereon, a soft, resilient, flexible plastic coating encasing said spring steel frame, and an artificial tooth mounted on each of said pins whereby the artificial teeth are held on said pins by said barbs.

2. A denture according to claim 1 in which apertures are defined in said flanges and said plastic coating extends through said apertures in said flanges, thereby locking said coating to said flanges.

3. A denture according to claim 2 in which said plastic coating surrounds the portions of said pins adjacent said opposite side of said base and said artificial teeth reside in abutment against said coating adjacent said opposite side of said base.

4. A denture according to claim 1 in which said flanges of said encased frame are formed so as to grip the gums of a wearer therebetween when worn.

5. A method of constructing dentures comprising:
constructing spring steel frames to conform to the gums of an intended denture wearer by die cutting said frames from spring steel stock so that said frames each have a curved base with pairs of flanges extending laterally outwardly therefrom at positions corresponding to the tooth positions of an intended wearer,
defining apertures in said flanges and defining non-circular apertures in said base at positions corresponding to missing tooth positions,
inelastically bending said flanges to diverge on one side of said base at angles conforming to the gum configuration of the intended wearer,
constructing pins with shanks having barbs thereon and having heads configured to fit into said non-circular apertures in said base so as to be immobilized from rotation relative to said base,
securing artificial teeth in a viscous, preheated state onto said pins and curing said teeth so that said barbs hold said artificial teeth fast,
inserting said pin heads into said base at said non-circular apertures corresponding to missing tooth positions so that said artificial teeth reside at positions corresponding to the missing tooth positions of an intended wearer and in spaced separation from said frame base,
molding a plastic material to form a resilient coating on said spring steel frames, which coating penetrates said apertures in said flanges and the interstices between said artificial teeth and said frame base, so that the exterior of said coating resembles the gums of the intended wearer, and
bending said flanges within said coating as required to conform to the mouth of an intended wearer.

6. A method according to claim 5 further comprising making a cast of an impression of the gums of an intended wearer, constructing a bench plate former to conform to said cast, and bending said flanges in said bench plate former.

7. A method according to claim 6 in which said flanges in the gum molar region and the interior flanges from incisor to incisor are bent prior to securing said pin heads in said frame bases using said bench plate former, and the exterior flanges from incisor to incisor are bent using said bench plate former after said pin heads are secured in said frames.

8. A method according to claim 5 further comprising using pliers with jaws having mating flat portions and mating curved portions to bend said flanges within said coating.

9. A method according to claim 5 further comprising forming said non-circular apertures in said base as geometric figures with at least some re-entering angles, and forming said pin heads with cross sections conforming to said geometric figures.

10. A method according to claim 9 further comprising securing said pin heads in said frame bases by locking said pin heads onto said base with transverse cotter pins.

* * * * *